US00PP16473P3

(12) United States Plant Patent
Larsen

(10) Patent No.: US PP16,473 P3
(45) Date of Patent: Apr. 25, 2006

(54) ***OSTEOSPERMUM* PLANT NAMED 'SUNNY PHILIP'**

(50) Latin Name: *Osteospermum ecklonis*
Varietal Denomination: Sunny Philip

(75) Inventor: Bjarne Nyholm Larsen, Odense (DK)

(73) Assignee: Sunny Osteospermum APS, Odense (DK)

( * ) Notice: Subject to any disclaimer, the term of this patent is extended or adjusted under 35 U.S.C. 154(b) by 35 days.

(21) Appl. No.: 10/873,295

(22) Filed: Jun. 23, 2004

(65) Prior Publication Data

US 2005/0039238 P1 Feb. 17, 2005

(30) Foreign Application Priority Data

Jul. 7, 2003 (QZ) ..... PBR 20031238

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Foley & Lardner, LLP

(57) ABSTRACT

A new distinct cultivar of *Osteospermum* plant named 'Sunny Philip', characterized by its large upright purple inflorescences; spatulate ray florets with colors: (upper surfaces) RHS 155A, white to RHS 87B, violet, at base and (underside) RHS 86C, violet to RHS 85D, violet at base; compact and bushy plant form, mainly due to upright stems; moderately vigorous growth habit, but less need for chemical growth retardation; and high number of large inflorescences per plant.

6 Drawing Sheets

Genus and species of the plant claimed: *Osteospermum ecklonis* (DC) T. Norl.
Variety denomination: 'Sunny Philip'.

BACKGROUND OF THE INVENTION

The present Invention relates to a new and distinct cultivar of *Osteospermum* plant, botanically known as *Osteospermum ecklonis* (DC) T. Norl., commonly known as Cape Daisy and hereinafter referred to by the variety denomination 'Sunny Philip'.

The new *Osteospermum* is a product of a planned breeding program conducted by the Inventor, Bjarne Larsen, in Stige, Denmark. The new *Osteospermum* originated from a controlled cross breeding made in May 2000 by the Inventor between *Osteospermum ecklonis* (DC) T. Norl. designated '3.122.983' (unpatented) and *Osteospermum ecklonis* (DC) T. Norl. designated '9913' (unpatented). The Inventor selected the new *Osteospermum* cultivar from the progeny of the above crossing in 2003 on the basis of its inflorescence color, size, and compact, freely branching habit. Plants of the new *Osteospermum* are upright, compact and have a unique color combination of upper and underside of the ray florets.

Asexual reproduction of the new cultivar by terminal cuttings taken and propagated at trial production batches in Stige, Denmark, has shown that the unique features of this new *Osteospermum* are stable and reproduced true to type in many successive generations.

SUMMARY OF THE INVENTION

The following traits have been repeatedly observed and are determined to be the unique characteristics of 'Sunny Philip'. These characteristics in combination distinguish 'Sunny Philip' as a new and distinct cultivar:

1. Large upright purple inflorescences;
2. Spatulate ray florets with colors: (upper surfaces) RHS 155A, white to RHS 87B, violet, at base and (underside) RHS 86C, violet to RHS 85 D, violet at base.
3. Compact and bushy plant form, mainly due to upright stems;
4. Moderately vigorous growth habit, but less need for chemical growth retardation; and
5. High number of large inflorescences per plant.

Plants of the cultivar 'Sunny Philip' can be compared to plants of the *Osteospermum ecklonis* (DC) T. Norl. Cultivar 'Sunny Zara' (unpatented). However, in side-by-side comparisons conducted by the Inventor in Stige Denmark, plants of the cultivar 'Sunny Philip' and the cultivar 'Sunny Zara' differ in the following characteristics:

1. Plants of the new *Osteospermum* have striking color combinations of white/violet ray florets and violet-blue disk with orange pollen.
2. Plants of the new *Osteospermum* have darker green leaves while plants of the cultivar 'Sunny Zara' have yellow-green-colored leaves.
3. Plants of the new *Osteospermum* are shorter and more compact than the plants of the cultivar 'Sunny Zara'.
4. Plants of the new *Osteospermum* have more inflorescences per plant than the plants of the cultivar 'Sunny Zara' as well as larger inflorescences.

Plants of the cultivar 'Sunny Philip' can be compared to plants of the parental cultivars '3.122.983' and '9913'. Plants of the cultivar 'Sunny Philip' differ from plants of the parental cultivars, '3.122.983' and '9913', primarily in inflorescence color.

Plants of the cultivar 'Sunny Philip' have not been observed under all possible environmental conditions. The phenotype may vary somewhat with variations in environment such as temperature, light intensity, day length, and fertility level without, however, any variance in genotype.

BRIEF DESCRIPTION OF THE PHOTOGRAPHS

The accompanying colored photographs illustrate the overall appearance of the new *Osteospermum* cultivar 'Sunny Philip' showing the colors as true as is reasonably possible with colored reproductions of this type. Colors in the photographs may differ slightly from the color values cited in the detailed botanical description which accurately describe the color of the new *Osteospermum* cultivar 'Sunny Philip'.

The first photograph shows a side perspective view of a typical flowering plant of 'Sunny Philip' as grown in an 11 cm pot.

The second photograph shows close-up, top view of the young and older inflorescences of 'Sunny Philip'.

The third photograph shows a close-up of an individual inflorescence of 'Sunny Philip'.

The fourth photograph shows a close-up of the back side of an individual inflorescence of 'Sunny Philip'.

The fifth photograph shows the detail of front and back of a 'Sunny Philip' inflorescence and young and older leaves.

The sixth photograph shows numerous 'Sunny Philip' plants as grown in the greenhouse.

DETAILED BOTANICAL DESCRIPTION

In the following description, color references are made to The Royal Horticultural Society Colour Chart (R.H.S.), $4^{th}$ edition. Plants were grown under greenhouse conditions. Plants used for this description were grown for about 20 weeks after cutting.

Botanical classification: *Osteospermum ecklonis* (DC) T. Norl.

Parentage:

*Female parent.*—*Osteospermum ecklonis* (DC) T. Norl. designated '3.122.98' (unpatented).

*Male parent.*—*Osteospermum ecklonis* (DC) T. Norl. designated '9913' (unpatented).

*Propagation.*—Type cutting terminal vegetative cuttings.

*Root description.*—Fine, well branched.

Plant description:

*Form.*—Perennial plant with upright plant habit. *Osteospermum* flowers in composite heads. Freely branching with lateral flowering branches forming at every node; dense and bushy.

*Crop time.*—After rooting, about 18 weeks are required to produce finished flowering plants in 11 cm pots.

*Plant height* (*soil level to top of plant plane*).—About 18 cm.

*Diameter.*—25 cm.

*Vigor.*—Moderately vigorous growth rate.

*Foliage description.*—Leaves alternate, single, lobed, obovate to spatulate shape, pinnate venation. Length: 3–10 cm. Width: Up to 50 mm. Apex: obtuse. Base: attenuate. Margin: broadly dentate. Texture: smooth, glabrous, shiny. Scattered short, stiff hairs. Color: Young foliage, upper and lower surfaces: RHS 137C and RHS 137D, green. Mature foliage, upper surfaces RHS 139A, green, lower surface RHS 139B, green.

*Petiole typical length.*—13 mm. Petiole observed length: 10–15 mm. Petiole diameter: 2–4 mm. Petiole color: center, RHS 149D, yellow-green; Shape: flat, winged petioles.

Inflorescence description:

*Inflorescence arrangement and shape.*—Tubular disk and ray florets in composite "pin-wheel" heads; with 15 parted involucre. Sturdy peduncles; peduncle length: 9–10 cm.

*Natural flowering season.*—Continuous throughout the spring and summer. Season can be extended by vernalization and long day treatments.

*Inflorescence longevity on the plant.*—Longevity of individual inflorescences is highly dependent on temperature and light conditions 5 to 10 days. Inflorescences persistent, ray florets folding and withering slowly.

*Inflorescence diameter.*—About 5 cm.

*Inflorescence depth.*—Typical: 6 mm. Observed: Composite capitulum 6 mm.

*Inflorescences.*—Ray Florets: Typical number of ray florets per inflorescence: 25. Observed number of ray florets per inflorescence: 23–26. Length: Ray florets: About 23 mm. Width (diameter): About 5 mm. Ray floret apex: spatulate, acute. Ray floret base: attenuate. Ray floret margin: entire. Ray floret color: Upper surfaces (when opening), RHS N155B, white, to RHS 85A, violet at base and edges; underside (when opening): RHS 86B, violet, to RHS 85D, violet at base. Upper surface (fully opened): RHS 155A, white, to RHS 87B, violet, at base; underside (fully opened): RHS 86C, violet to RHS 85D, violet, at base.

*Disk florets.*—Typical number of disks florets per inflorescence: 60. Observed number of disks florets per inflorescence: 50–70. Length: About 3 mm. Width (diameter): About 1 mm. Disk florets overall shape:. Disk floret free tips apex: Attenuate. Disk floret base: Fused. Disk floret margin: free tips entire. Disk floret color: Upper surfaces: RHS N92D, violet-blue; underside: RHS 86C, violet, to translucent RHS 155A, white.

*Peduncle.*—Strength: Moderately strong. Length: About 9–10 cm. Diameter: About 2 mm. Color: RHS 144C, yellow-green.

*Phyllary.*—Observed number of phyllaries: 13–16. Typical number of phyllaries: 15. Length: 6–12 mm. Width: 1–3 mm. Overall shape: lanceolate. Apex shape: acuminate. Base shape: fused. Margin: entire. Color: Upper surface: RHS 141C, green edges translucent; lower surface: RHS 141B, green.

Reproductive organs:

Androecium:

*Location.*—Disc florets only.

*Anthers.*—Linear, fused, stamen color RHS 202A, black, pollen RHS 16A, yellow-orange.

Gynoecium:

*Location of gynoecium.*—Ray and disc florets.

*Typical pistil number.*—1. Observed pistil number: 1. Style and stigma, color RHS 155A, white and RHS 201A, black, respectively.

*Seed.*—Length: About 1 mm. Diameter: About 0.3 mm.

Disease/pest resistance: Good.

Disease/pest susceptibility: Low.

Weather tolerance: Plants of the new *Osteospermum* have exhibited good tolerance to draught, rain. Temperature down to −1° C. (30° F.).

I claim:

1. A new and distinct cultivar of *Osteospermum* plant named 'Sunny Philip', as illustrated and described herein.

* * * * *

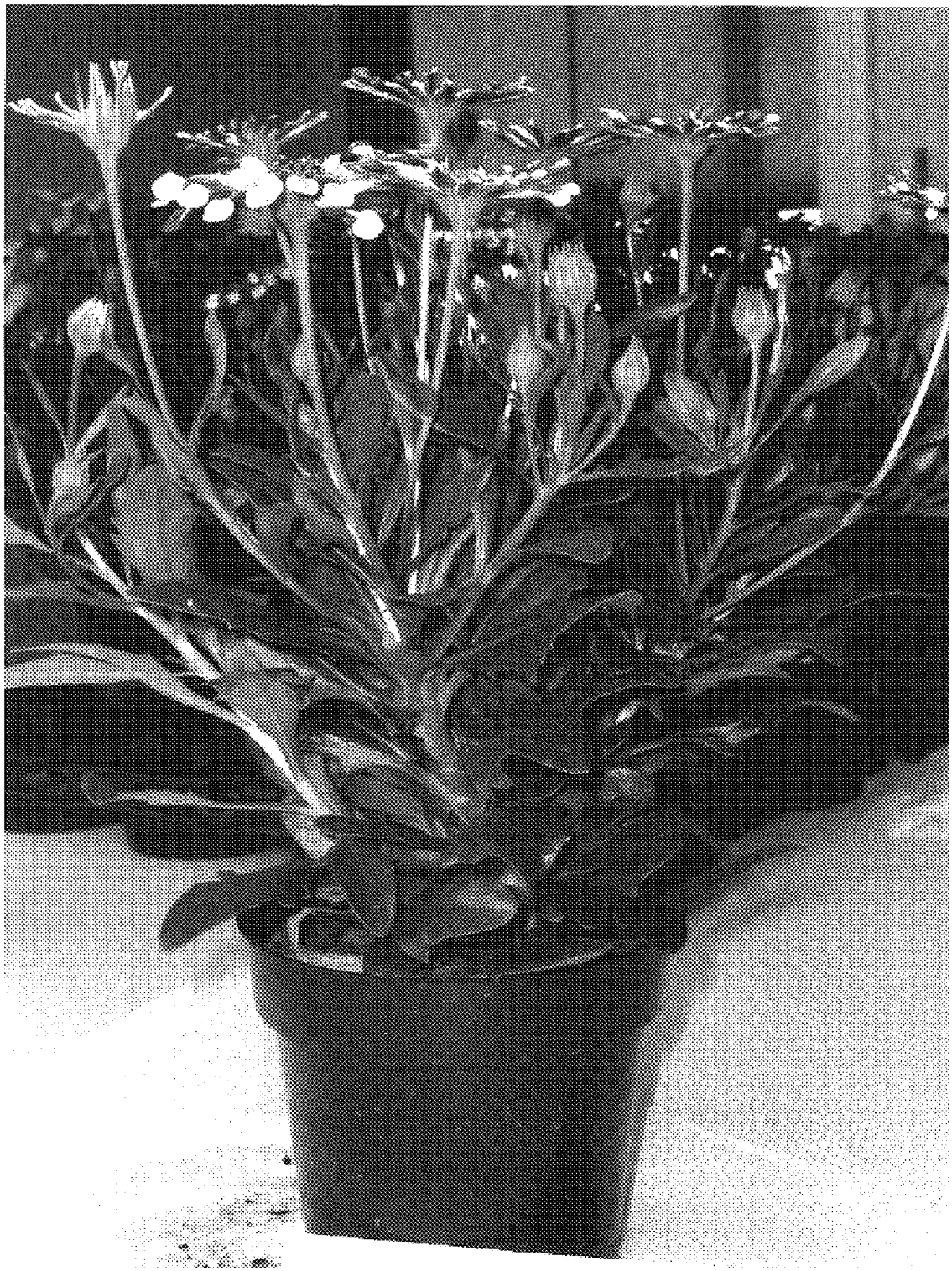

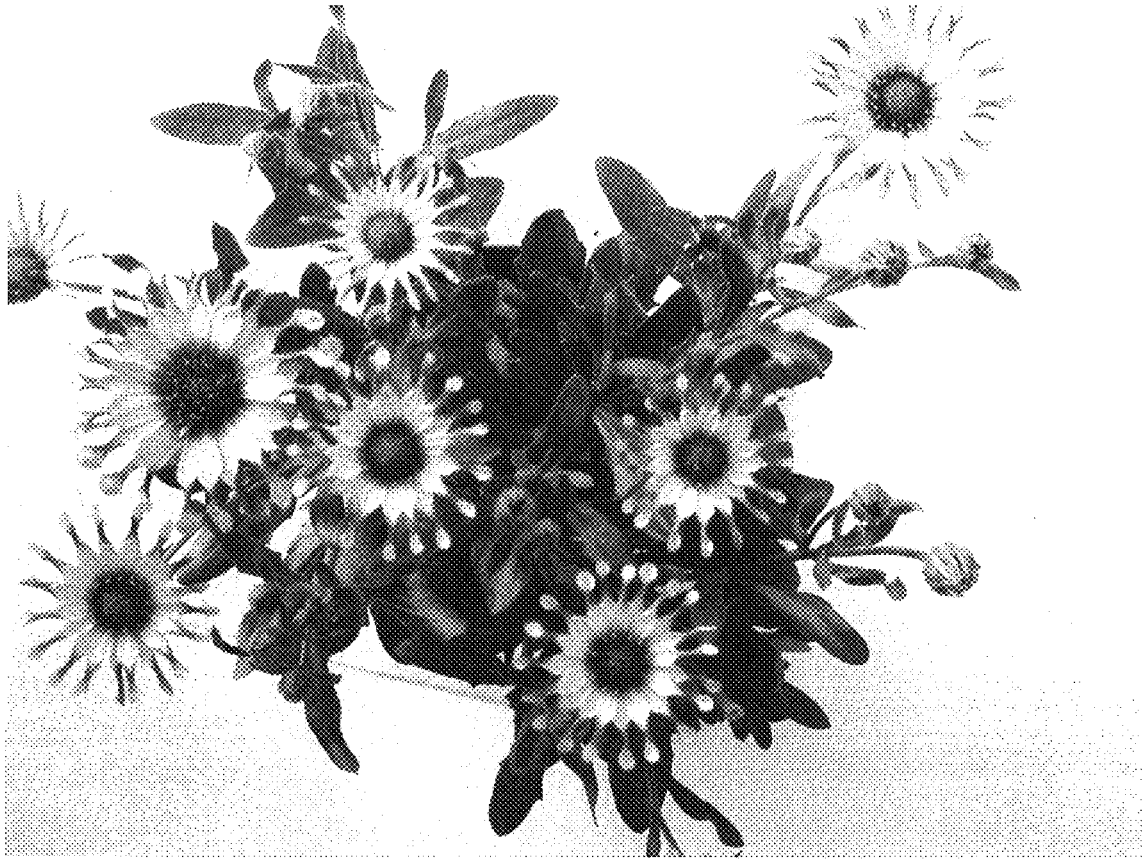

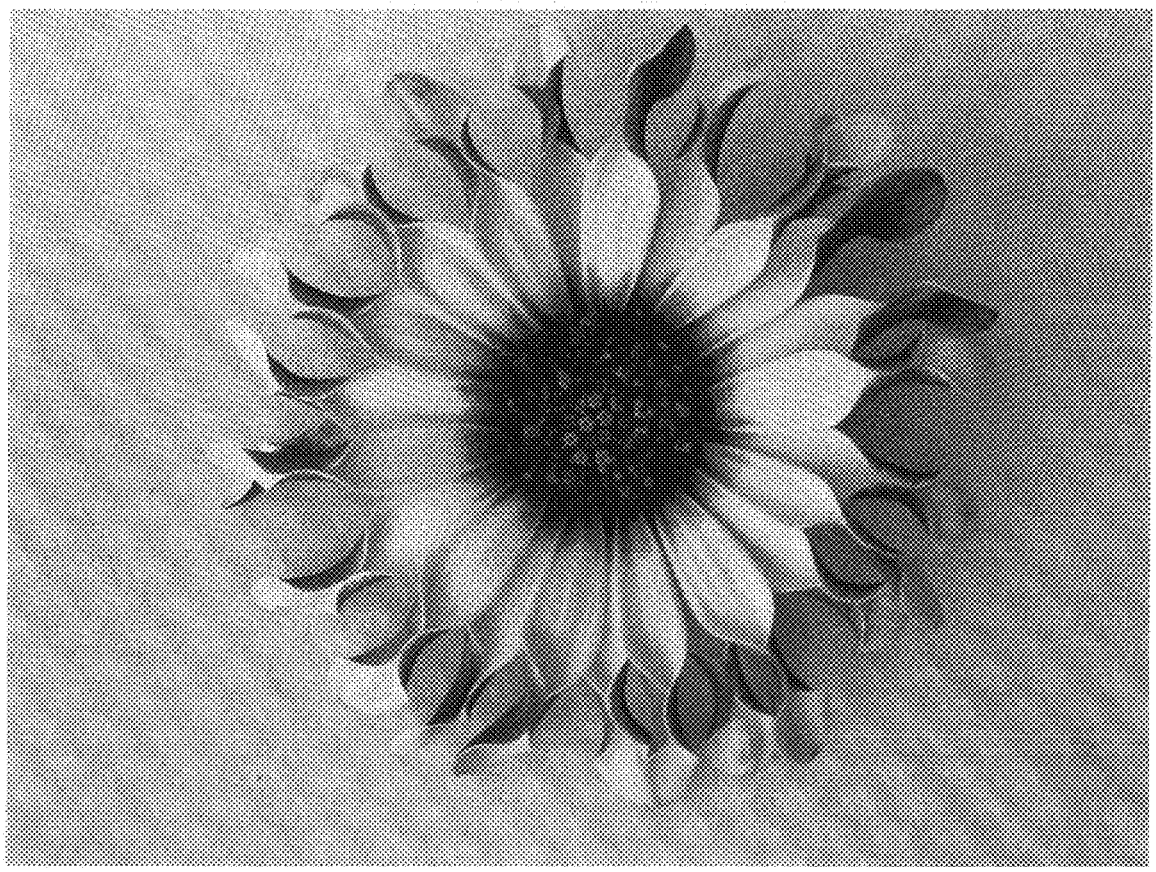

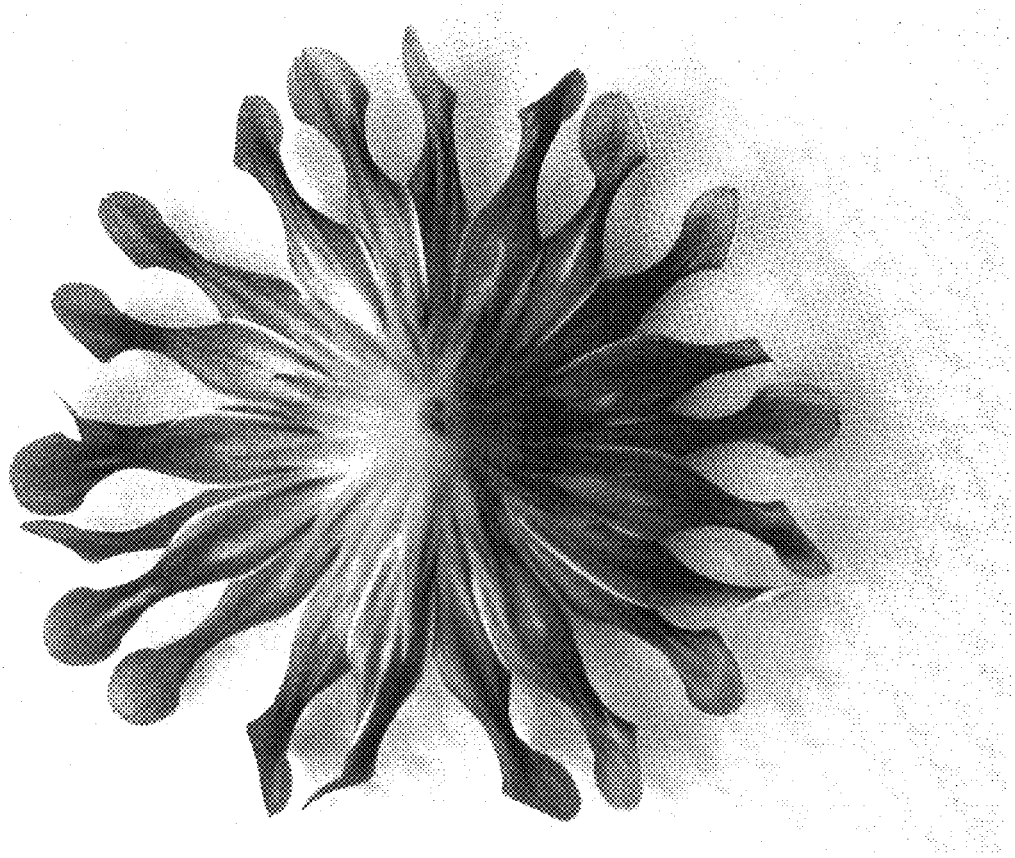

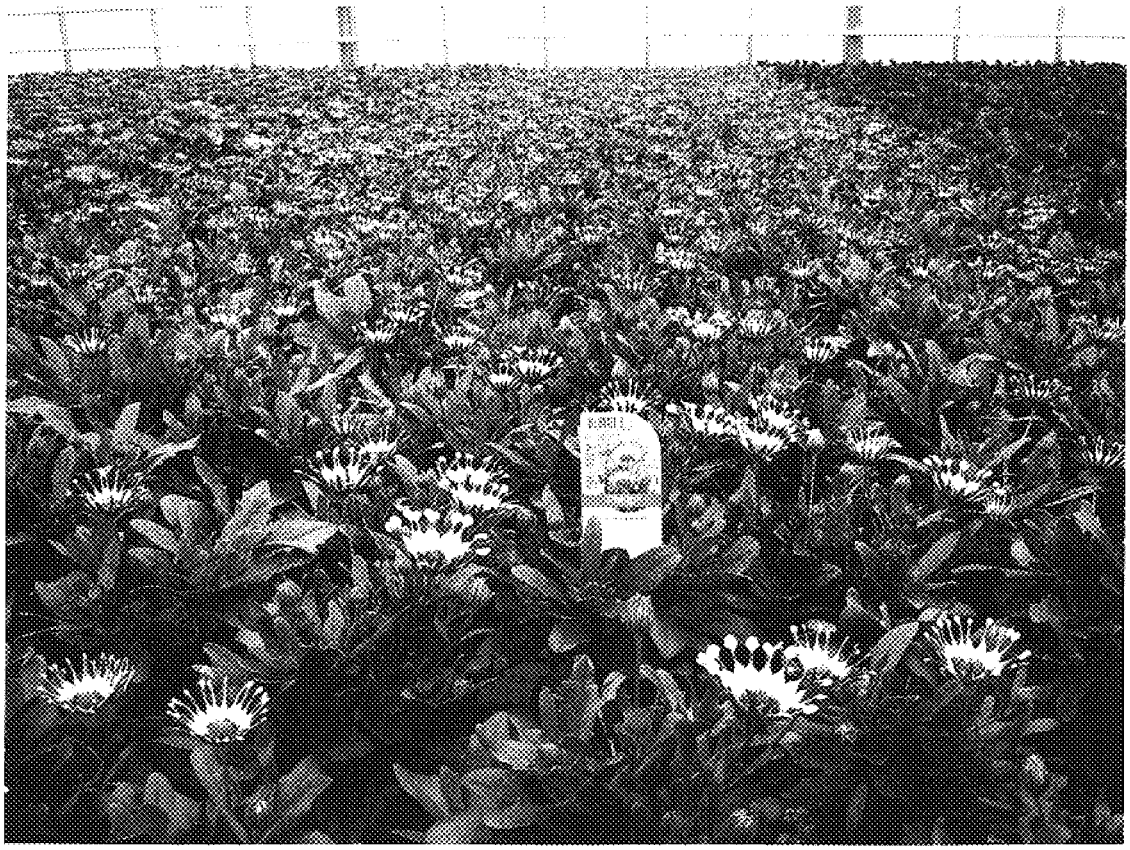

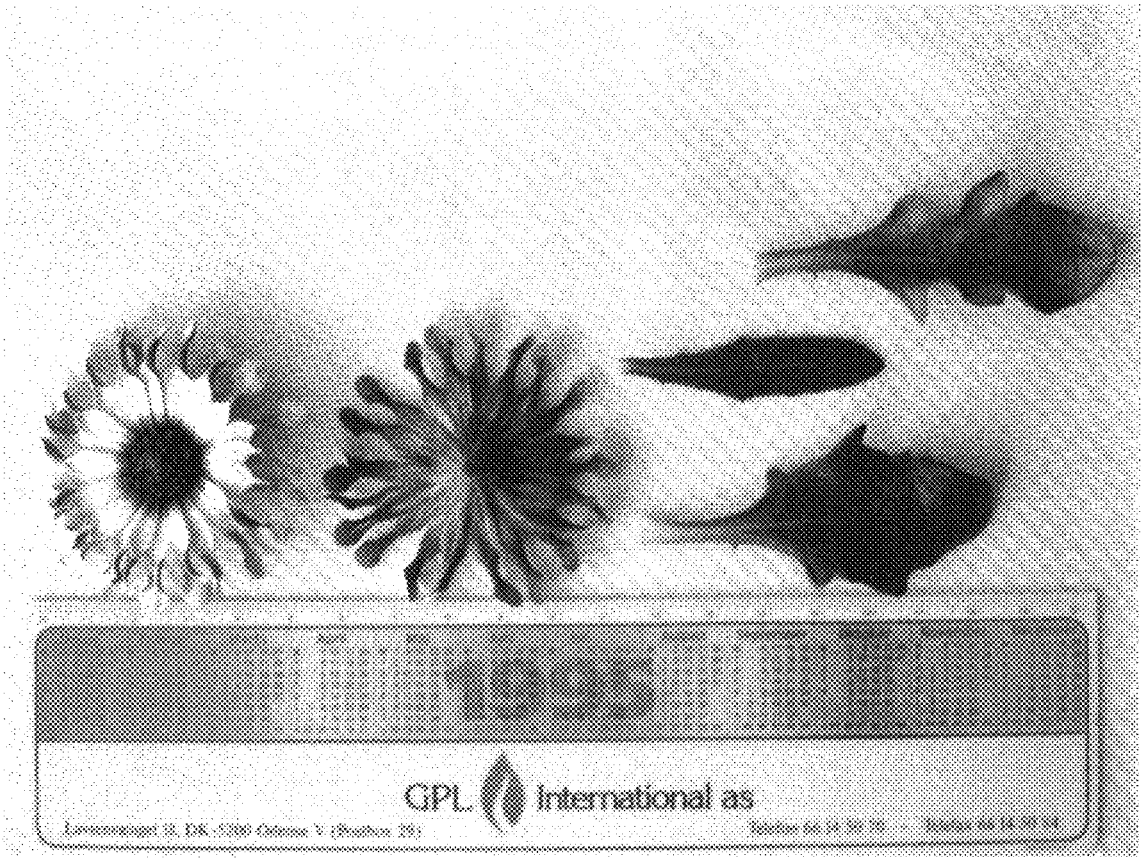
GPL International as